(12) United States Patent
Ferenczi et al.

(10) Patent No.: US 7,907,990 B2
(45) Date of Patent: Mar. 15, 2011

(54) SYSTEMS, METHODS AND APPARATUS FOR ONCOLOGY WORKFLOW INTEGRATION

(75) Inventors: Lehel M. Ferenczi, Budapest (HU); Márta Fidrich, Szeged (HU)

(73) Assignee: General Electric Company, Schenectady, NY (US)

( * ) Notice: Subject to any disclaimer, the term of this patent is extended or adjusted under 35 U.S.C. 154(b) by 995 days.

(21) Appl. No.: 11/464,836

(22) Filed: Mar. 24, 2006

(65) Prior Publication Data

US 2007/0238951 A1    Oct. 11, 2007

Related U.S. Application Data

(60) Provisional application No. 60/743,770, filed on Mar. 24, 2006.

(51) Int. Cl.
*A61D 6/00* (2006.01)
(52) U.S. Cl. .................................. 600/427; 600/436
(58) Field of Classification Search .............. 600/407, 600/425, 427, 401, 410, 420, 431, 436, 437; 382/131; 128/920
See application file for complete search history.

(56) References Cited

U.S. PATENT DOCUMENTS

| | | | |
|---|---|---|---|
| 2003/0097068 A1* | 5/2003 | Hossack et al. | 600/443 |
| 2006/0030768 A1* | 2/2006 | Ramamurthy et al. | 600/407 |
| 2006/0085223 A1* | 4/2006 | Anderson et al. | 705/2 |
| 2007/0081704 A1* | 4/2007 | Pan et al. | 382/128 |
| 2007/0129627 A1* | 6/2007 | Profio et al. | 600/407 |
| 2009/0010514 A1* | 1/2009 | Kimura | 382/131 |

* cited by examiner

*Primary Examiner* — Tse Chen
*Assistant Examiner* — Rochelle Reardon
(74) *Attorney, Agent, or Firm* — Dean Small; The Small Patent Law Group

(57) ABSTRACT

A non-transitory computer-accessible medium having executable instructions capable of directing a processor to generate a spatio-temporal maximum-intensity projection from a respiratory phase separated series of images; generate a phase separated four-dimension series of images of various modalities, generate a radiation therapy structure set, and generate a radiation therapy plan, store the spatio-temporal maximum-intensity projection, the respiratory phase separated series of images, the phase separated four-dimension series of images of various modalities, the radiation therapy structure set, and the radiation therapy plan in a memory, receive a selection of a custom range of phase separated series, display a four-dimension phase cine of the custom range of phase separated series having the spatio-temporal maximum-intensity projection, identify a desired phase series for diagnosis and treatment planning, and store the radiation therapy structure set and the radiation therapy plan in the memory.

9 Claims, 14 Drawing Sheets

SYSTEMS, METHODS AND APPARATUS FOR ONCOLOGY WORKFLOW INTEGRATION

RELATED APPLICATIONS

This application claims the benefit of U.S. Provisional Application Ser. No. 60/743,770 filed Mar. 24, 2006 under 35 U.S.C. 119(e).

U.S. Original application Ser. No. 11/352,514; filed on Feb. 11, 2006 titled "SYSTEMS, METHODS AND APPARATUS OF HANDLING STRUCTURES IN THREE-DIMENSIONAL IMAGES" is incorporated herein by reference.

U.S. Original application Ser. No. 11/352,477; filed on Feb. 11, 2006 titled "SYSTEMS, METHODS AND APPARATUS OF HANDLING STRUCTURES IN THREE-DIMENSIONAL IMAGES HAVING MULTIPLE MODALITIES AND MULTIPLE PHASES" is incorporated herein by reference.

U.S. Original application Ser. No. 10/711,189; filed on Aug. 31, 2004 titled "SYSTEM AND METHOD FOR GENERATING A DIGITAL IMAGE OF AN INTERNAL ANATOMY OF A PERSON" is incorporated herein by reference.

U.S. Provisional Application Ser. No. 60/415,992, filed October 2002, titled "RETROSPECTIVE RESPIRATION GATES METHODS AND APPARATUS" is incorporated herein by reference.

U.S. Original application Ser. No. 10/678,839; filed on Oct. 3, 2003 titled "SYSTEMS AND METHODS FOR IMPROVING USABILITY OF IMAGES FOR MEDICAL APPLICATIONS" is incorporated herein by reference.

FIELD OF THE INVENTION

This invention relates generally to imaging systems, and more particularly to workflow of imaging systems.

BACKGROUND OF THE INVENTION

During acquisition of image with conventional computer tomography (CT) and conventional positron emission tomography (PET) scanners, the images scanned in consecutive table positions could correspond to different respiratory phases. Images that correspond to different respiratory phases have blurred regions and staged effects on 3D models that can be created from the images, which reduces quality of the images and the models. The blurred regions and staged effects have the effect of increasing the difficulty of visually identifying and/or detecting the organ edges, because these organs can have considerable movements due to the patient's breathing even for consecutive table positions.

Multi-phase imaging is imaging in four dimensions— length, width, height and time, commonly known as 4D. Before the introduction of 4D imaging technology in oncology applications, to compensate for the organ movements during a breathing cycle of a patient being imaged, a considerable margin was added around the target volume. These additional margins have considerably increased the risk of radiation injuries to the surrounding healthy organs, and in the same time reduced the efficiency of the radiation dose delivered to a tumor that is the subject of the imaging.

In addition, conventional oncology workflow is cumbersome and complicated. Conventional oncology workflow requires a considerable number of steps in multi-phase imaging. In addition, the current workflow cannot support CT/PET scanners, and 4D PET images. Though there are several solutions and applications, which support loading and spatially matching of the images with different modalities, even with contouring support, there is no process to review the final treatment plan using all the modality images involved during the treatment planning. Multi-phase imaging also requires a superfluous number of applications from scanning to diagnosis and treatment.

Multi-modality imaging is the implementation of two of more imaging modalities to generate images of patient's anatomy or functionality. The multi-modality images are suitable for diagnostic purposes or radiotherapy treatment, or for surgical planning. Examples include conventional X-ray plane film radiography; computed tomography (CT) imaging, magnetic resonance imaging (MRI); and nuclear medicine imaging techniques, such as positron emission tomography (PET) and single photon emission computed tomography (SPECT).

Comparison and use of multi-modality images improves the detection of tumors, especially in case of brain cancers and soft tissues, when the neighbor organs have almost similar CT densities (Hounsfield units), or when the tumor is inside the organ. Due to these advantages there is an increasing need from the oncology departments to provide better detection methods and automated tumor and cell disease diagnosis.

Conventional TPS can load only CT images. The conventional TPS systems are able to load only Radiation Therapy Structure Set (RTSS) objects with reference to a single series.

The conventional TPS systems and other systems permit the definition of MIP, Average IP and MinIP images based on the images of a series having different spatial coordinates. Other external applications are able to define MIP, Average IP and Min IP image series based on the images for the same table location, but corresponding to different respiratory phases. However, conventional systems do not provide for treatment plan (i.e. radiation therapy plan RTPL) definition that includes flexibility to define and redefine the images based on the different separation parameters. These images are important to detect the organ movements between the maximum and minimum positions of the organs, regions of interest during the respiratory cycle, to define the margins required during non-gated treatment.

For the reasons stated above, and for other reasons stated below which will become apparent to those skilled in the art upon reading and understanding the present specification, there is a need in the art for improved identification of tumors and fewer steps in the process of image acquisition, diagnosis and treatment. There is also a need in the art to reduce the risk of radiation injuries to the surrounding healthy organs. There is also a need in the art for treatment plan definition that includes flexibility to define and redefine the images based on the different separation parameters. There is also a need in the art for a TPS that can load more than CT images and Radiation Therapy Structure Set (RTSS) objects with reference to a single series.

BRIEF DESCRIPTION OF THE INVENTION

The above-mentioned shortcomings, disadvantages and problems are addressed herein, which will be understood by reading and studying the following specification.

In one aspect, an integrated treatment planning system (TPS) includes a treatment planning component that receives a four-dimension computer tomography (four-dimension computed-tomography) file. Treatment planning component also generates radiation therapy structure set/radiation therapy plan and generates a reference to at least one image.

The integrated TPS also includes a four-dimensional integration component that receives a respiratory-motion file and receives a raw four-dimension file. The integrated TPS also includes a multi-modality component coupled to the treatment planning component and a spatial registrar that is coupled to the treatment planning component to generate a series of multi-modality images from one of a four-dimension computed-tomography positron-emission-tomography image, a computed-tomography/positron-emission-tomography four-dimension positron-emission-tomography computed-tomography image, a magnetic-resonance image, a computed-tomography image and a positron-emission-tomography image. The integrated TPS improves identification of tumors in fewer steps in the process of image acquisition, diagnosis and treatment, reduces the risk of radiation injuries to the surrounding healthy organs, implements treatment plan definition that includes flexibility to define and redefine the images based on the different separation parameters.

Systems, clients, servers, methods, and computer-readable media of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

The detailed description is divided into five sections. In the first section, a system level overview is described. In the second section, embodiments of methods are described. In the third section, the hardware and the operating environment in conjunction with which embodiments may be practiced are described. In the fourth section, particular implementations are described. Finally, in the fifth section, a conclusion of the detailed description is provided.

System Level Overview

Figure 1:
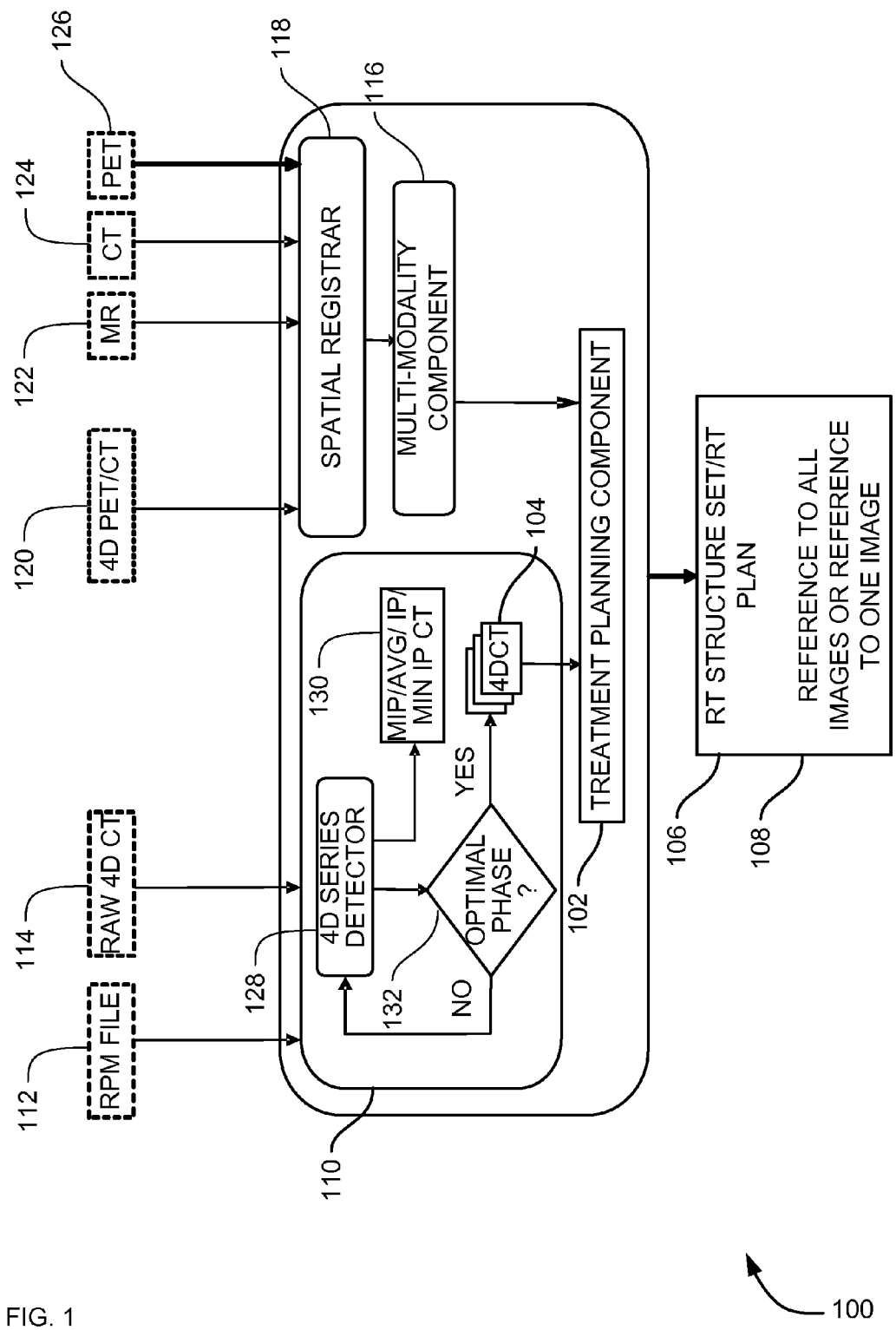
FIG. 1 is a diagram illustrating a system-level overview of an embodiment.

FIG. 1 is a block diagram of an overview of an integrated treatment planning system (TPS) 100. Integrated TPS 100 solves the need in the art for improved identification of tumors and fewer steps in the process of image acquisition, diagnosis and treatment and reduced risk of radiation injuries to the surrounding healthy organs. Integrated TPS 100 solves the need in the art for a TPS that can load more than CT images and Radiation Therapy Structure Set (RTSS) objects with reference to a single series.

The integrated TPS 100 is operable to identify and load all the image series referenced by the Radiation Therapy Structure Set (RTSS) object, even if the image series are from different patients, exams, have different geometries and/or have different orientations.

The integrated TPS 100 includes a treatment planning component 102 that is operable to receive a four-dimension computer tomography (4DCT) file 104. Treatment planning component 102 is also operable to generate radiation therapy structure set/radiation therapy plan 106. Treatment planning component 102 is also operable to generate a reference to at least one image 108.

The integrated TPS 100 also includes a four-dimensional integration component 110 that is operable to receive a respiratory-motion (RPM) file 112 and is operable to receive a raw 4D file 114. A RPM file 112 is a file containing data that describes respiratory motion of the patient during imaging. In one embodiment of measuring the respiratory motion, the inhalation/exhalation air volume is measured. In another embodiment of measuring the respiratory motion, a small cube is placed on the chest of patient during imaging and the movement of the cube is captured by a camera placed alongside with the patient's head-feet direction.

The integrated TPS 100 also includes a multi-modality component 116 that is operably coupled to the treatment planning component 102. Integrated TPS 100 also includes a spatial registrar 118 that is operably coupled to the treatment planning component 102 to generate a series of multi-modality images from one of a 4D CT PET image, a DLS/DS 4D PET/CT image 120, a MR image 122, a CT image 124 and a PET image 126. Thus, the integrated TPS 100 can load multi-modality images. A DLS/DS file is one embodiment of a computed-tomography/positron-emission-tomography (CT/PET) image. One example of an image scanner that generates a DLS/DS image is the Discovery LightSpeed™ CT/PET scanner manufactured by General Electric Company of Stamford, Conn.

In some embodiments, the four-dimensional integration component 110 includes a 4D series detector 128, a maximum/IP-average/IP-minimum/IP component 130 that is operably coupled to the 4D series detector 128 and an optimal phase determiner 132 that is operably coupled to the 4D series detector 128.

In some embodiments, the integrated TPS 100 is an integrated oncology diagnostic workflow system. Oncology workflow integration that uses multi-modality images and/or raw images that are matched with respiratory phase information to the treatment plan.

The integrated TPS 100 can load images of any of the described file types, such as RPM file 112, raw 4D 114, DLS/DS 4D PET/CT image 120, MR image 122, CT image 124, and PET image 126, but loading any particular file type is not required. In some embodiments, at least one CT image series 124 file is loaded.

While the integrated TPS 100 is not limited to any particular treatment planning component 102, 4DCT file 104, radiation therapy structure set/radiation therapy plan 106, image 108, four-dimensional integration component 110, RPM file 112, raw 4D file 114, multi-modality component 116, spatial registrar 118, DLS/DS 4D PET/CT image 120, MR image 122, CT image 124, PET image 126, 4D series detector 128, maximum/IP-average/IP-minimum/IP component 130 and optimal phase determiner 132. However, for sake of clarity a simplified treatment planning component 102, 4DCT file 104, radiation therapy structure set/radiation therapy plan 106, image 108, four-dimensional integration component 110, RPM file 112, raw 4D file 114, multi-modality component 116, spatial registrar 118, DLS/DS 4D PET/CT image 120, MR image 122, CT image 124, PET image 126, 4D series detector 128, maximum/IP-average/IP-minimum/IP component 130 and optimal phase determiner 132 are described.

Figure 14:
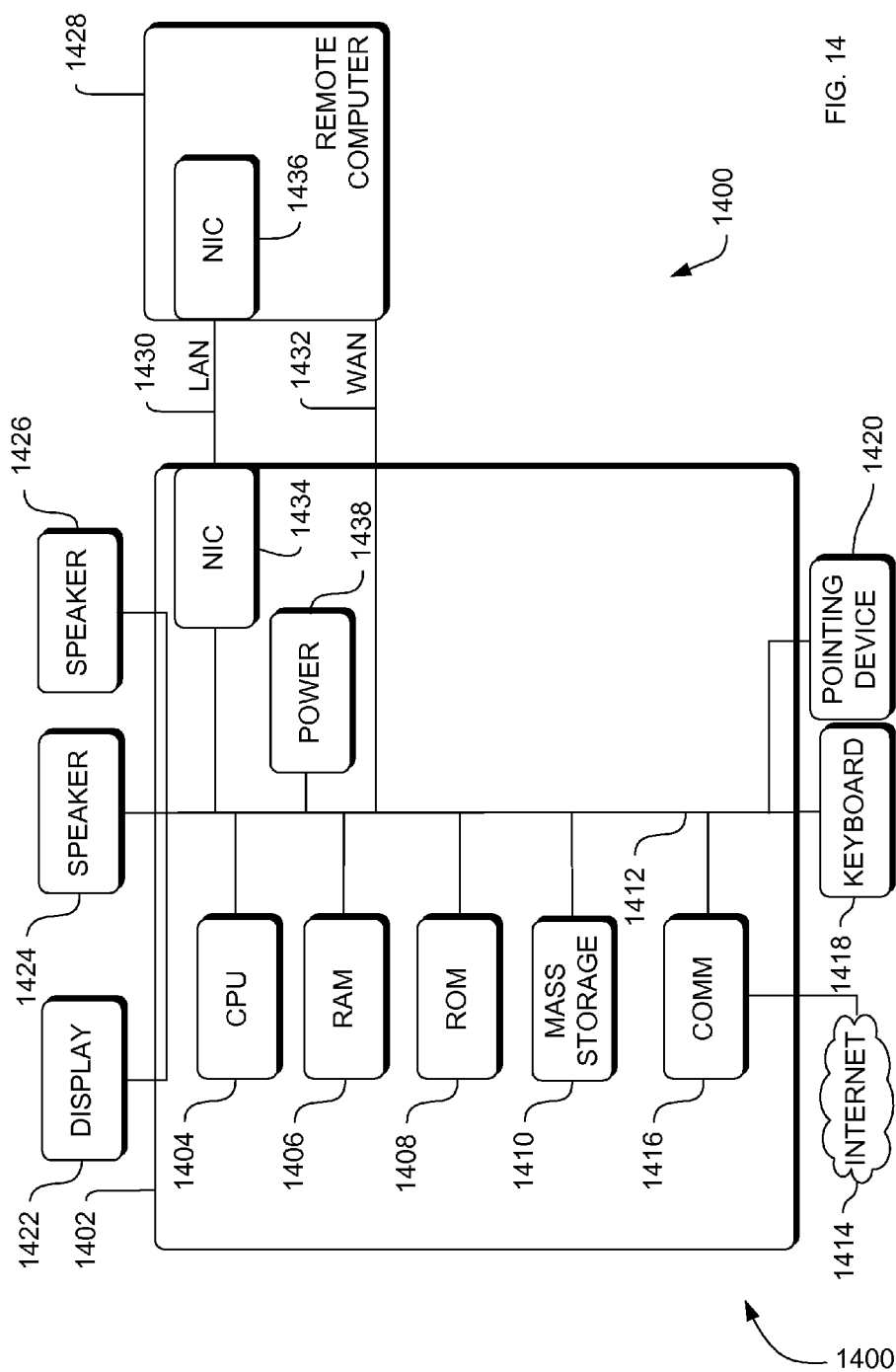
FIG. 14 is a block diagram of the hardware and operating environment in which different embodiments can be practiced.

Some embodiments operate in a multi-processing, multi-threaded operating environment on a computer, such as computer 1402 in FIG. 14. For example, the treatment planning component 102, four-dimensional integration component 110, multi-modality component 116, spatial registrar 118, 4D series detector 128, maximum/IP-average/IP-minimum/IP component 130 and optimal phase determiner 132 can be embodied as computer hardware circuitry or as a computer-readable program, or a combination of both. In another embodiment, integrated TPS 100 is implemented in an application service provider (ASP) system.

More specifically, in a computer-readable program embodiment, the programs can be structured in an object-orientation using an object-oriented language such as Java, Smalltalk or C++, and the programs can be structured in a procedural-orientation using a procedural language such as COBOL or C. The software components communicate in any of a number of means that are well-known to those skilled in the art, such as application program interfaces (API) or inter-process communication techniques such as remote procedure call (RPC), common object request broker architecture (CORBA), Component Object Model (COM), Distributed Component Object Model (DCOM), Distributed System Object Model (DSOM) and Remote Method Invocation (RMI). The components execute on as few as one computer as in computer 1402 in FIG. 14, or on at least as many computers as there are components.

Method Embodiments

In the previous section, a system level overview of the operation of an embodiment is described. In this section, the particular methods of such an embodiment are described by reference to a series of flowcharts. Describing the methods by reference to a flowchart enables one skilled in the art to develop such programs, firmware, or hardware, including such instructions to carry out the methods on suitable computers, executing the instructions from computer-readable media. Similarly, the methods performed by the server computer programs, firmware, or hardware are also composed of computer-executable instructions. Methods 200-900 are performed by a program executing on, or performed by firmware or hardware that is a part of, a computer, such as computer 1402 in FIG. 14.

Figure 2:
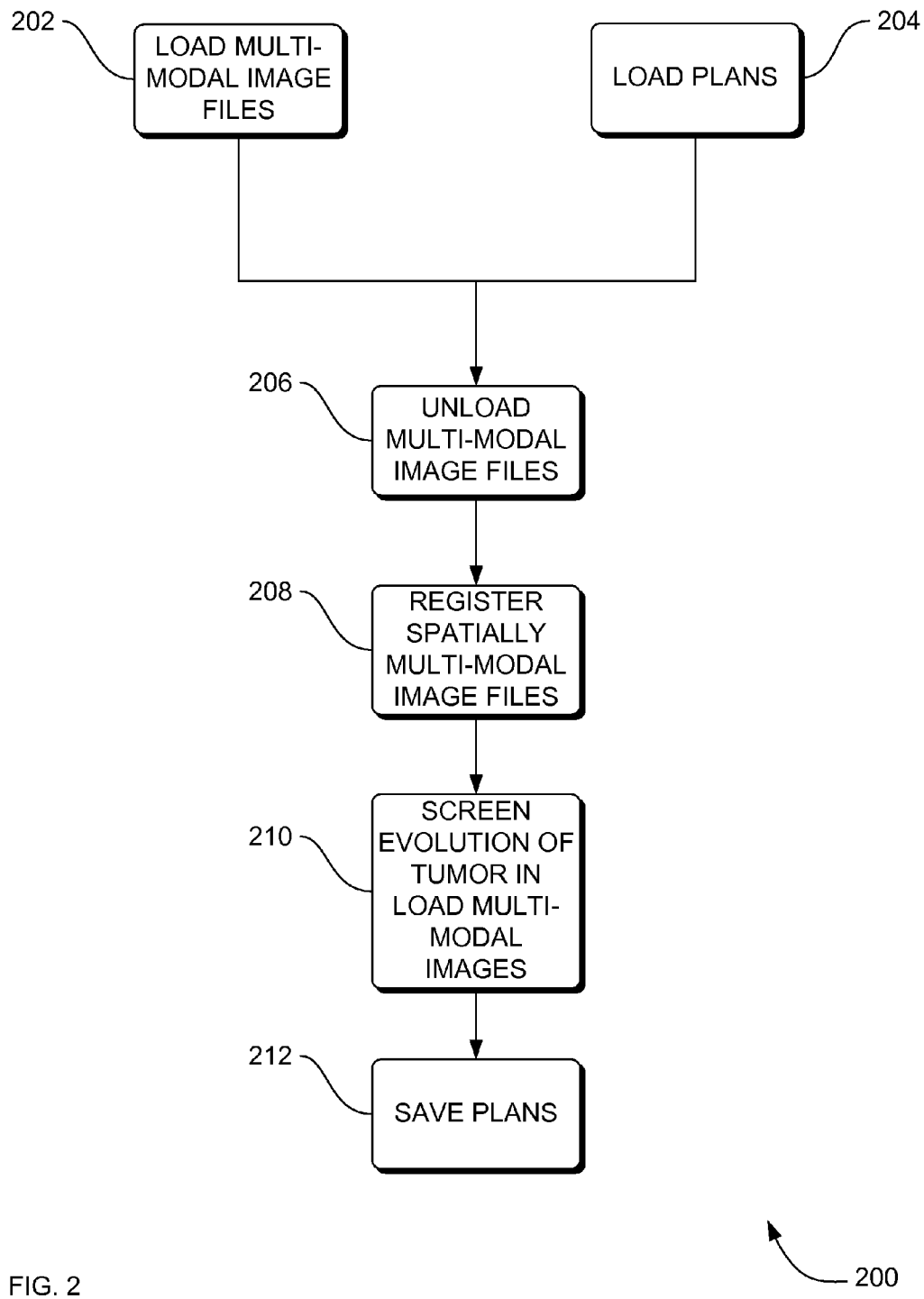
FIG. 2 is a flowchart of a method to perform image multi-modality functions according to an embodiment.

FIG. 2 is a flowchart of a method 200 to perform image multi-modality functions according to an embodiment. Method 200 solves the need in the art to improved identification of tumors and fewer steps in the process of image acquisition, diagnosis and treatment and reduced risk of radiation injuries to the surrounding healthy organs.

In some embodiments, method 200 includes loading 202 DICOM files of various modalities, the modalities further comprising computed tomography (CT), positron emission tomography (PET), magnetic resonance (MR), four dimension (4D) CT, 4D PET, and 4D CT/PET. Thus, method 200 can load multi-modality images also, providing tools for the user to switch the display between these image series.

Figure 10:
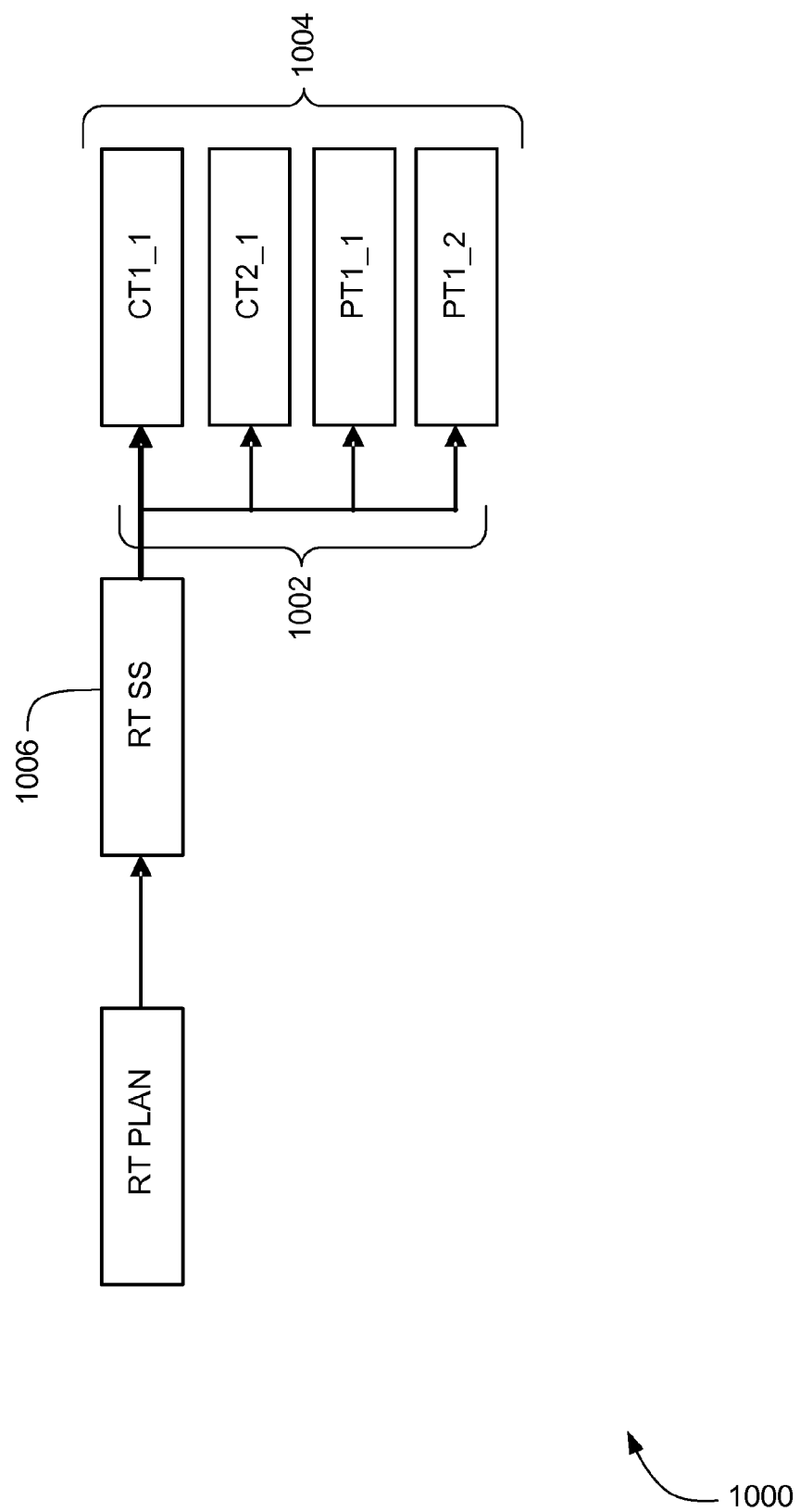
FIG. 10 is a diagram of a data structure for use in managing multi-modality and multi-phase image series, according to an embodiment.

In some embodiments, method 200 also includes loading 204 a RTSS and a RT plan (RTPL) in reference to one or more series of images. Thus, method 200 loads all the image series referenced by the RTSS object, even if the series are from different patients, exams, have different geometries and/or orientations. FIG. 10 below provides additional information on the relationship of the image series.

In some embodiments, method 200 also includes unloading 206 the image series. For situations where the user accidentally loads an image series which is not necessary for planning or diagnosis, method 200 provides the unloading action 206 unload a selected series of images. The unloaded series is erased from the system. If the series selected for unload was a reference series, another image series must be selected as the reference series before the un-load can be performed.

In some embodiments, method 200 also includes registering 208 a spatially multi-modality image series. Examples of multi-modality image series include a CT-CT image series, a CT-MR image series, and a CT-PET image series. When image series with mismatching geometries and orientations are loaded 208 during operation of method 200, then automatic registration can be displayed to the user. Conventional Registration processes can be implemented in action 208.

In some embodiments, method 200 also includes screening 210 an evolution of a tumor using multi-modality images and comparison-functions between exam, with highlighting of the tumor evolution. The screening can be accomplished by scanning the image series at different times, and by loading and comparing the RTPL and RTSS for the same patient in different exams and different times. This action 208 improves a possibility of detecting the tumor evolution and also allows reuse and transfer of images of the previously defined organs and other region of interest from an older RTSS to the current session.

In some embodiments, method 200 also includes saving 212 the RTSS and the RTPL.

Figure 3:
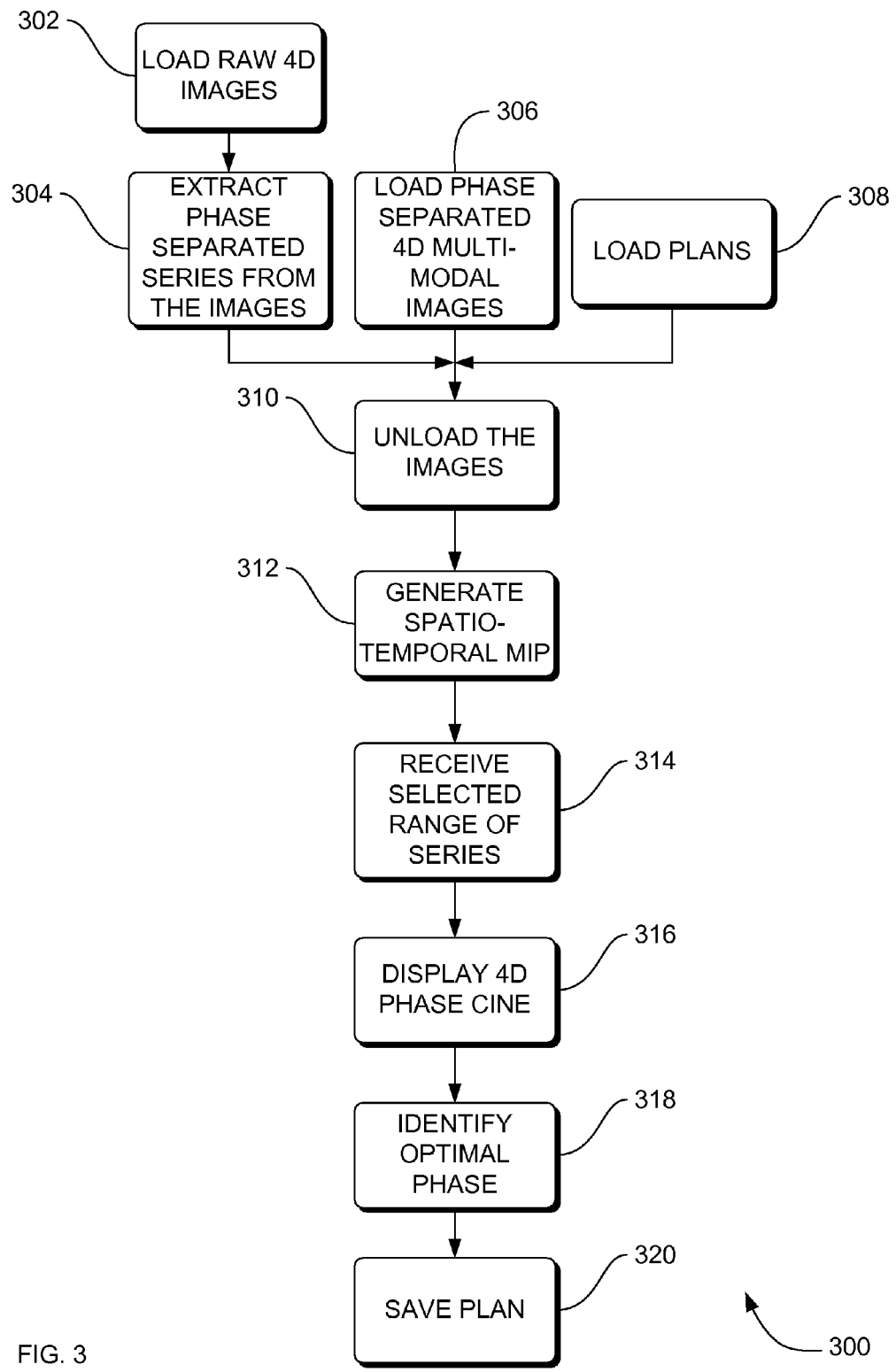
FIG. 3 is a flowchart of a method to perform image multi-phase functions according to an embodiment.

FIG. 3 is a flowchart of a method 300 to perform image multi-phase functions according to an embodiment. Method 300 solves the need in the art for treatment plan definition that includes flexibility to define and redefine the images based on the different separation parameters.

Method 300 includes loading 302 raw 4D image series of various modalities and motion information from one or more external systems. In some embodiments, the modalities include 4D CT and 4D PET. One example of an external system is a respiratory motion (RPM) system by Varian Corporation of Palo Alto, Calif. The raw 4D image series and motion information provides integration of existing image separation features into method 200 and the support for the respiratory motion information.

In some embodiments, method 300 also includes extracting 304 images into a respiratory phase separated series, based on respiratory motion information from one or more external systems. One example of an external system is a respiratory motion (RPM) system by Varian Corporation of Palo Alto, Calif. Images extracted into respiratory phase separated series provides temporal review and redefinition of parameters used for 4D phase series separation. In some embodiments, the user can immediately review the result of the separation after the separation parameters are set, and if the result meets expectations of the user, to declare the images and continue the workflow, without switching to another application. If the results of the image separation based on respiratory phase information do not meet the expected results, then the user without quitting, can drop the current result, redefine the separation parameter and redo the instant review.

In some embodiments, method 300 also includes loading 306 phase separated 4D images of various modalities, the modalities further comprising 4D CT, 4D PET, and 4D CT/PET. If images that have been previously separated by other external applications (Ex. Advantage™ 4D, CT console, CT/PET console) are selected as input, then the images are loaded. Depending on the initial selection, if the images are loaded in one step or in separate steps, the images can be linked in 4D cine loops or not. In some embodiments, an interface to the integrated TPS system provides tools to change the linking between 4D series.

In some embodiments, method 300 also includes loading 308 a RTSS and a RTPL in reference to one or more multiple series. In some embodiments, the multiple series are all series used for planning or diagnose.

In some embodiments, method 300 also includes unloading 310 the image series.

In some embodiments, method 300 also includes generating 312 at least one of a spatio-temporal maximum-intensity projection (MIP), an average intensity projection (IP), and a minimum IP. The generating is based partly on a custom range of table positions or respiratory phases. Thus, method 300 solves the need in the art for treatment plan definition that includes flexibility to define and redefine the images based on the different separation parameters. These images are instrumental in detecting the organ movements between the maximum and minimum positions of the organs, regions of interest during the respiratory cycle, to define the margins required during non-gated treatment. During non-gated treatment the patient breath freely, the radiation is not stopped, but irradiates a larger region, to cover not only the tumor extensions, but the organ movement too. One embodiment of generating 312 is described in method 400 in FIG. 4 below.

In some embodiments, method 300 also includes receiving 314 a selection of a custom range of phase separated series and displaying 316 a 4D phase cine. Selection of the range of phase separated series and displaying the 4D phase cine assists in detecting motion of an imaged tumor during the respiratory phase. Sometime during a portion of respiratory cycle, some organs move a considerable distance, but during the remaining portions of the respiratory cycle, the organs move very little, if at all. Selection of the range of phase separated series and displaying the 4D phase cine can reduce the unimportant cycle parts from the 4D phase cine cycle, after which the user can concentrate on the cycle part, when the organ moves considerably.

In some embodiments, method 300 also includes identifying 318 an optimal phase series for diagnosis and treatment planning. The 4D respiratory cine cycle can be stopped at any phase and also the user is able to cycle manually between the phases one-by-one, and to review the organ and tumor positions each to other. These functions improve detection of the optimal phase during gated treatment, when the vital organs are less irradiated or are in a proper position for treatment. During gated treatment the patient respiratory cycle is observed in same manner like during scanning and the beam radiation is enabled only when the patient is in the selected respiratory cycle.

In some embodiments, method 300 also includes saving 320 the RTSS and the RTPL. In particular, the RTSS and the RTPLs are saved with reference to all series used for planning or diagnose.

In method 300, the extracting 304, the loading of the phase separated 4D images 306 and the loading of the RTSS and the RTPLs 308 can be performed in any order relative to each other. For example, in some embodiments, the extracting 304, the loading 306 and the loading 308 are performed simultaneously. In all variations of the order of performance, the extracting 304, the loading 306 and the loading 308 are completed before unloading of the image 310.

Figure 4:
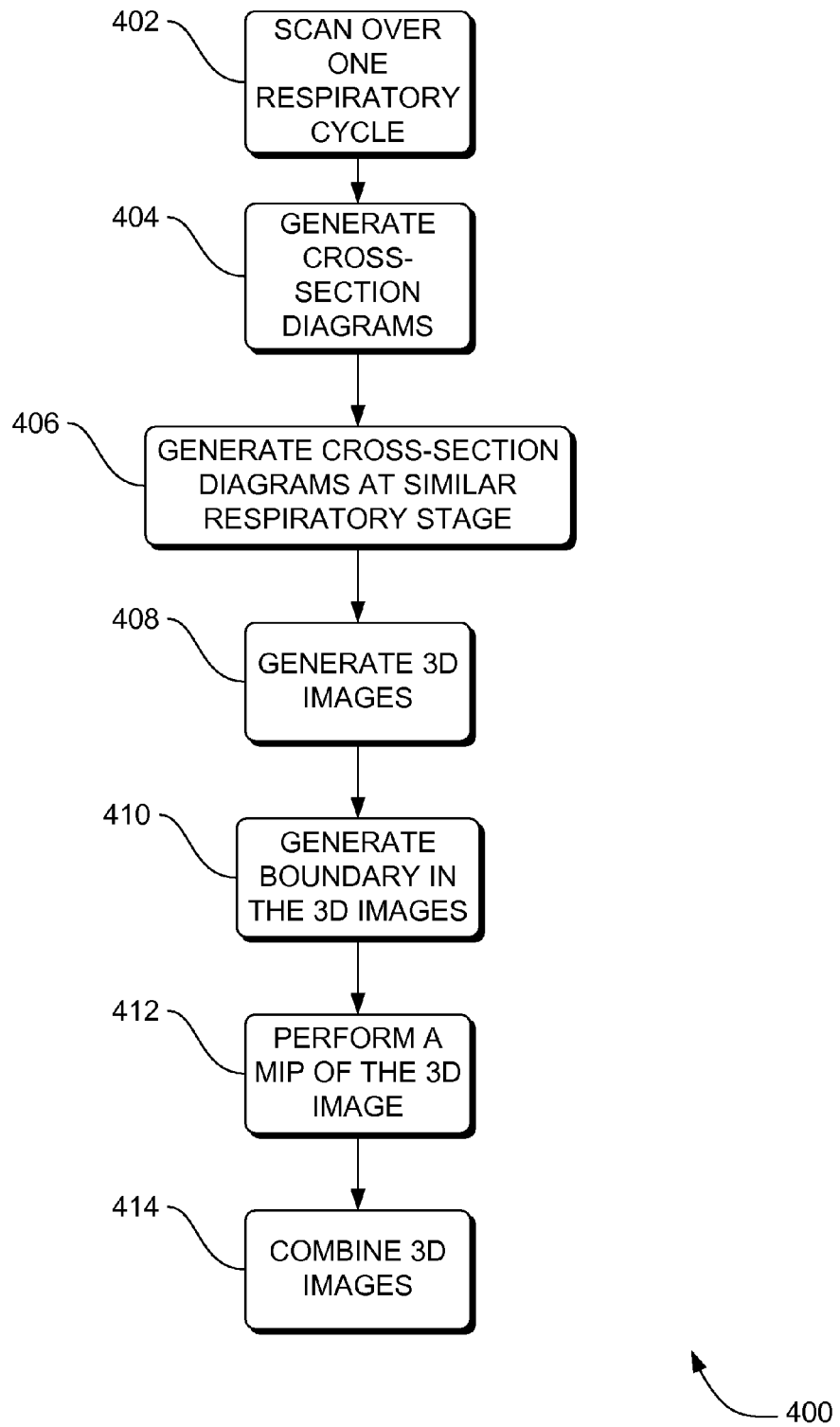
FIG. 4 is a flowchart of a method of generating spatio-temporal information, according to an embodiment.

FIG. 4 is a flowchart of a method 400 of generating spatio-temporal information, according to an embodiment. Method 400 is one embodiment of generating spatio-temporal information in action 312 in FIG. 3 above. Method 400 solves the need in the art to improved identification of tumors and fewer steps in the process of image acquisition, diagnosis and treatment and reduced risk of radiation injuries to the surrounding healthy organs.

Some embodiments of method 400 includes scanning 402 the internal anatomy of the person at a plurality of positions along an axis to obtain scanning data. The scanning at each position is performed over one or more one respiratory cycles of the patient. Some embodiments of method 400 includes generating 404 a plurality of cross-sectional digital images based on the scanning data. Some embodiments of method 400 includes generating 406 a plurality of cross-sectional digital image groups, each group comprising at least two digital images of the plurality of cross-sectional digital images wherein each of the two digital images indicate the internal anatomy at a substantially similar respiratory state. Some embodiments of method 400 includes generating 408 a plurality of 3-D digital images, wherein each digital image of the plurality of 3-D digital images is determined from a corresponding one of the plurality of cross-sectional digital image groups performing a maximum intensity projection of the plurality of 3-D digital images to obtain a first 3-D digital image. Some embodiments of method 400 includes generating 410 a boundary within the first 3-D digital image around a predetermined portion of the internal anatomy of the person. Some embodiments of method 400 includes performing 412 a minimum intensity projection of the predetermined portion of the first 3-D digital image to obtain a second 3-D digital image. Some embodiments of method 400 also includes combining 414 the first 3-D digital image and the second 3-D digital image to obtain a final 3-D digital image.

Figure 5:
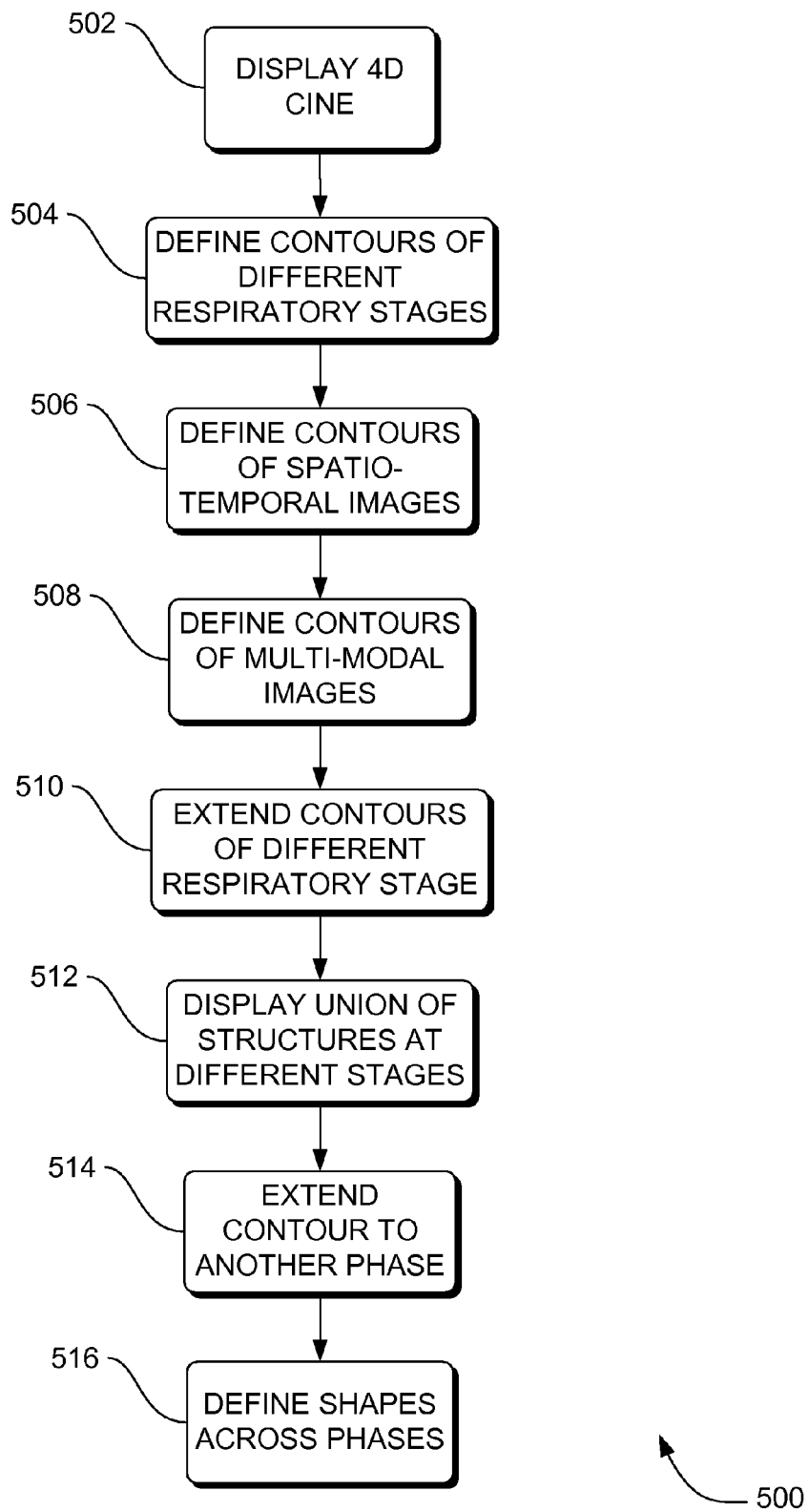
FIG. 5 is a flowchart of a method to contour images, according to an embodiment.

FIG. 5 is a flowchart of a method 500 to contour images, according to an embodiment. Method 500 solves the need in the art for contouring support with review of the final treatment plan using a variety of image modalities.

Method 500 includes displaying 502 a 4D cine of the images including contour definition and overlaying. Displaying 502 provides definition of the contours of a structure while behind the contour tool a 4D cine cycle is displayed. Thus, the user can visualize during contour definition whether or not the shape of the contour properly covers the organ movement in the corresponding table position for example across the respiratory phase cycles.

Some embodiments of method 500 also include defining 504 contours and overlaying the contours on images that correspond to different respiratory phases and a same table position.

Some embodiments of method 500 also include defining 506 contours on custom spatio-temporal maximum-intensity (MIP) projection; average-intensity projection (IP) and minimum-intensity-projection images (MIN). This function provides definition contours overlaid on MIP, Average IP and Min IP images.

Some embodiments of method 500 also include defining 508 contours and overlaying the contours on fused images (CT/PET and CT/MR) and on multi-modal images. Defining 508 contours and overlaying the contours on fused images on multi-modal images provides definition in one example of the contours based on a PET image, where the tumors are highlighted with different color codes and overlay this contour on the CT image to check the position and shape of the newly defined or modified contour on this modality also.

Some embodiments of method 500 also include extending 510 contours to each image of a series of images corresponding to different respiratory phase. The contours defined on a given respiratory phase can be overlaid on images corresponding to other respiratory phase, the contour can be saved into a different structure, after the corresponding modifications are made based on the current image. This function provides a kind of "copy-and-paste" functionality from one contour to another. Please see the detailed description of FIG. 12 below for additional information.

Some embodiments of method 500 also include displaying 512 a union of structures defined in different phases for a region of interest. Displaying the union of structures provides margin tools of the union. In some embodiments, the unions and margins are not saved until the user does not commit the unions and the structures. In some embodiments, the margins are extended and eroded in a preview mode.

Some embodiments of method 500 also include extending 514 automatic contour definition and segmentation processes to another phase series. The extending 512 can be performed with or without invocation by the user. In some embodiments, extending 514 includes generating automatically the structures of segmentation algorithms for each 3D model generated from image series corresponding to different respiratory cycles. The result of the segmentation or automatic structure definition algorithms can be reviewed in 4D cine cycles and also overlaid on different images. The names of the structures can identify the series models on which the structure was defined, and the user has an option to overlay a selected contour on any of the loaded series. For example: if the result of the segmentation or automatic contour definition algorithm is: struct1. If the segmentation is started on a multitude of series models (Ex. CT1_1, CT1_2 . . . ), then the corresponding structure names are: struct1_CT1_1, struct1_CT1_2 . . . and so on.

Some embodiments of method 500 also include defining 516 basic shapes having a common seed point and additional points provide across a plurality of phases. Some embodiments of defining basic shapes 516 includes defining a multitude of structures having basic shapes like: circle, ellipse, rectangle, polygon, etc. where the user can define a common starting point on a single phase, and give the additional points one-by-one one the other phases.

Figure 6:
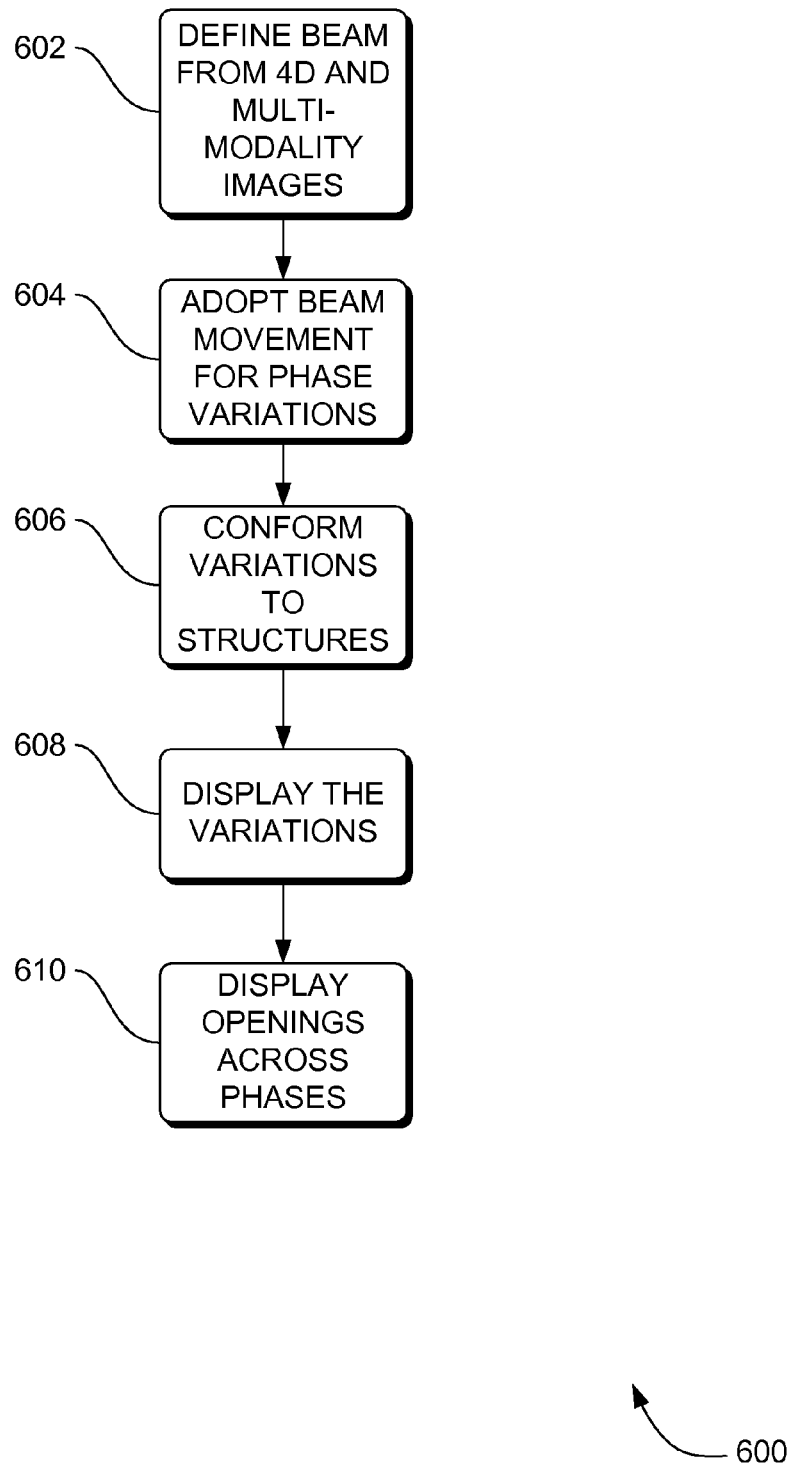
FIG. 6 is a flowchart of a method to perform beam handling of images, according to an embodiment.

FIG. 6 is a flowchart of a method 600 to perform beam handling of images, according to an embodiment. Some embodiments of method 600 include defining 602 a beam from a 4D image and a series of multi-modality images. Defining 602 the beam provides display of the DRR for several series: multi-modality and multi-phase series. The user can decide based on the DRR information which phase series to use for treatment, and also can check the beam conformation on different DRRs, manually adjust the collimators on the DRR.

Some embodiments of method 600 also include adopting 604 the beam movement for phase variations to visualize irradiated parts of the patient for each of a number of phases. Having DRR images corresponding to different respiratory phases displayed in 4D cine loop, the variation of organ shapes and positions can be detected on the DRR directly. The user can detect directly on the DRR if the beam will affect vital organs during a non-gated treatment.

Some embodiments of method 600 also include conforming 606 variation of the beam to structures defined for the region of interest and across phases also include displaying 608 the variation. In some embodiments, conforming 606 includes defining structures of organs, tumors or other region of interest on each series from a respiratory cycle, conforming the beams in each cycle and reviewing the beam collimator variations across a 4D cine movie.

Some embodiments of method 600 also include displaying 610 a maximum opening and a minimum opening for the beam across the phase variations. Displaying 610 the openings provides a visual record of the maximum and minimum openings of collimators and provides statistics to the user during a 4D cine loop.

Figure 7:
FIG. 7 is a flowchart of a method to digitally-reconstruct radiogram management of images, according to an embodiment.

FIG. 7 is a flowchart of a method 700 to digitally-reconstruct radiogram management of images, according to an embodiment. Method 700 includes digitally-reconstructing 702 a series of multi-modality and multi-phase radiogram images. In some embodiments, this reconstruction includes the generation of DRR images not only from CT images, but also from multi-modality images. Multi-phase DRR consist from the display of DRR images in 4D loop sequences, where the user has the option of observing the organ movement on the DRR images corresponding to different respiratory phases. Thus, method 700 provides functions to display the DRR for PET and MR image series.

Figure 8:
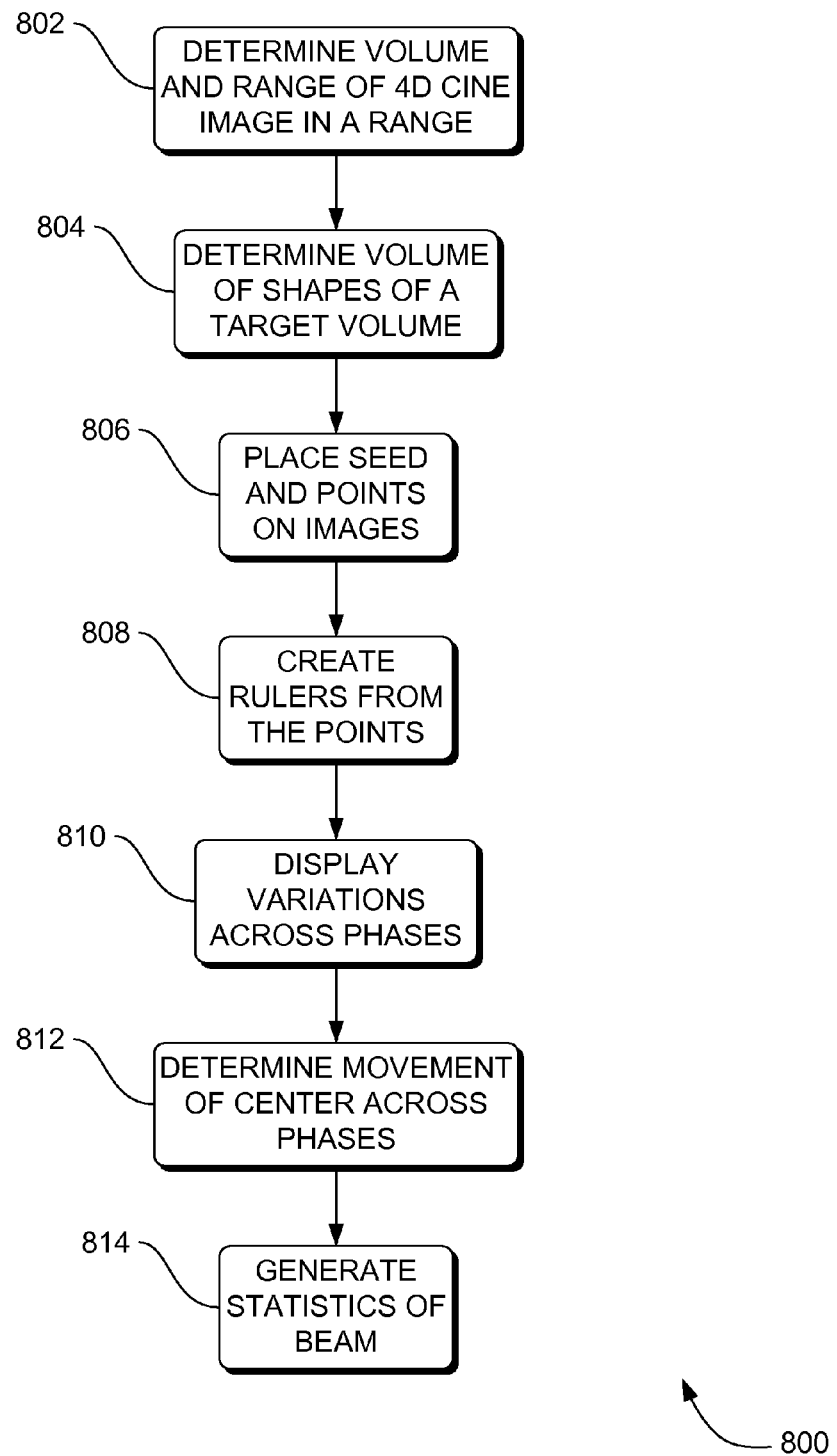
FIG. 8 is a flowchart of a method to manage images, according to an embodiment.

FIG. 8 is a flowchart of a method 800 to manage images, according to an embodiment. Some embodiments of method 800 include determining 802 a volume and a variation of cine 4D images from a selected range of respiratory phase separated images. Some embodiments of method 800 also include determining 804 the outer, and inner area and volume of spheres, cubes, and ellipsoids that contain or are in a target volume. Some embodiments of method 800 also placing 806 a first seed on an image and second points of a rulers on different images and then automatically creating the rulers from this point and display the length variations across phases.

Some embodiments of method 800 also creating 808 rulers from the points. In some embodiments, creating the rulers from the points includes actively measurement tools by placing a first seed on one image and a second point of the ruler on different images. Some embodiments of method 800 also displaying 810 length variations across the phases.

Some embodiments of method 800 also include determining 812 movement of a center of gravity of objects across phases also include generating 814 statistical measurements of an irradiated area for a beam across phases.

Figure 9:
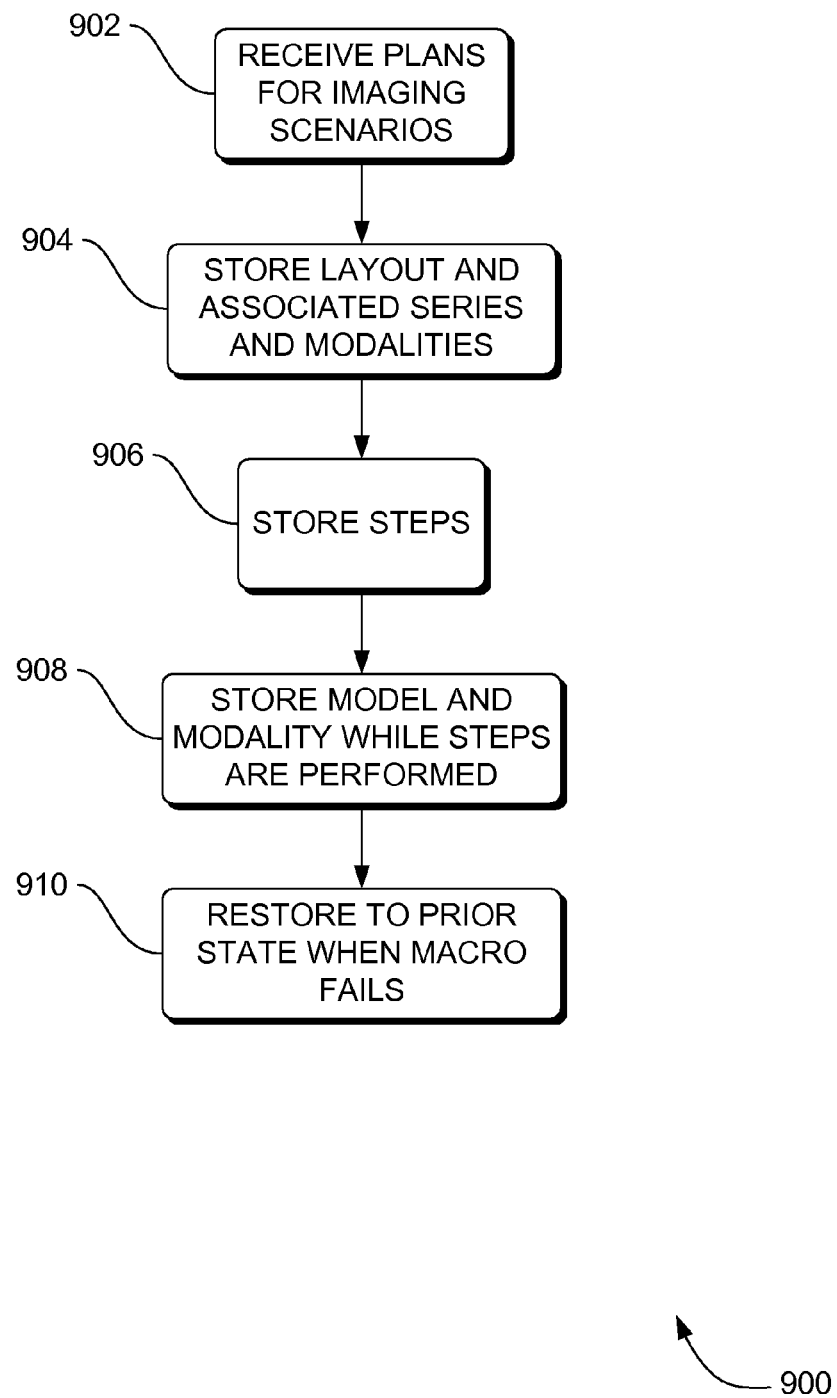
FIG. 9 is a flowchart of a method to manage customization, templates, macros of image processing according to an embodiment.

FIG. 9 is a flowchart of a method 900 to manage customization, templates, macros of image processing according to an embodiment.

In some embodiments, method 900 includes receiving 902 user-definitions of RTPLs for clinical imaging scenarios and method 900 includes storing 904 a view layout and associated series and modalities of the view. In some embodiments, user defined RTPL templates for typical clinical scenarios (Ex. Prostate cancer) are used to store the view layout information, the series and modalities attached to views. An example of view layout setup is shown below in the FIG. 13, with a two display configuration. This setup can be saved in the RTPL and in the template plans generated during the planning session. If the RTPL is loaded later, the same setup can be redisplayed with the corresponding series attached to views. The difference between RTPLs in the situation of plan templates is that, the system can restore the same view layout setup, but since the loading of series can be done in several steps and not all the series in same number of steps can be loaded eventually, the system can try to assign during load the series to corresponding views, at least the modality can be taken into account. If no series matches the current view layout setup, then the reference series can be assigned to the corresponding view.

In some embodiments, method 900 includes storing 906 a sequence of steps as a batch process, recording 908 a model and a modality upon which the macro is performed, while the macro is performed, and restoring 910 the system to a state prior to performance of the macro if the macro fails. The storing 906, recording 908 and restoring 910 involve macros with multi-modality and multi-phase support. Thus, method 900 provides a utility to record the sequence of steps into a batch process, which can be later reused. More specifically, method 900 provides ability to store which action step on which model, with what modality was performed. If the macro execution will fail, then the system will be returned to the state prior the macro execution start.

In some embodiments, methods 200-900 are implemented as a computer data signal embodied in a carrier wave, that represents a sequence of instructions which, when executed by a processor, such as processor 1404 in FIG. 14, cause the processor to perform the respective method. In other embodiments, methods 200-900 are implemented as a computer-accessible medium having executable instructions capable of directing a processor, such as processor 1404 in FIG. 14, to perform the respective method. In varying embodiments, the medium is a magnetic medium, an electronic medium, or an optical medium.

Implementations

Referring to FIGS. 10-13, particular implementations are described.

FIG. 10 is a diagram of a data structure 1000 for use in managing multi-modality and multi-phase image series, according to an embodiment. Simulation of multi-modality and multi-phase image series includes references 1002 to multiple image series 1004. In data structure 1000, a multi-modality and multi-phase series 1004 is referenced 1002 by an RTSS object 1006, even if the series 1004 is from different patients, exams, have different geometries and/or orientations. Data structure 1000 can be loaded as described above in action 202 in FIG. 2.

Figure 11:
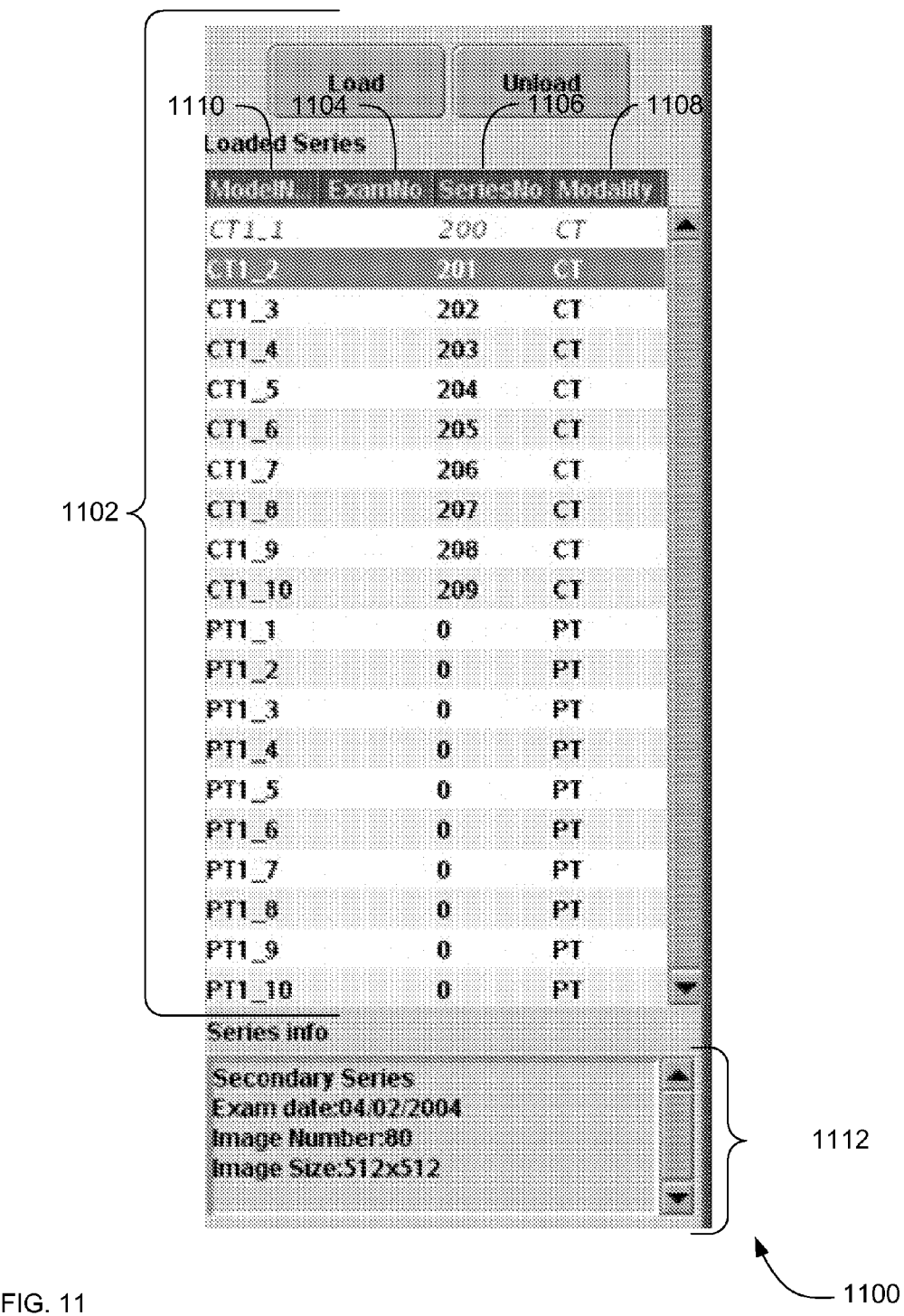
FIG. 11 is a diagram of a data structure for use in managing multi-modality and multi-phase image series, according to an embodiment.

FIG. 11 is a diagram of a data structure 1100 for use in managing multi-modality and multi-phase image series, according to an embodiment. In some embodiments, the data structure 1100 is a table, such as table 1102 shown in FIG. 11.

Table 1100 includes a number of fields, such as a field 1104 storing data representing an examination identification, and a field storing data representing a patient identification (not shown), a field 1106 storing data representing an image series number, a field 1108 storing data representing a modality, and a field 1110 storing data representing a unique identifier (UID) for each series, wherein no other series with a same unique identifier exists in a current plan.

To support multi-modality and multi-phase series images in an integrated oncology application, information about the loaded series can be displayed in the table 1102, where along with the important information about the loaded series (e.g. Exam ID 1104, Patient ID/Name, Series Number 1106, modality 1108) a UID 1110 will be defined for each series. The uniqueness of this identifier UID 1110 will be assured on plan level, in which no other series with the same identifier 1110 exists in the current plan.

In some embodiments of data structure 1102, below the table 1102 in a loaded series is a graphical information box 1112 with the additional details about the currently selected series in the table 1102. An identifier is visible for the user in the table 1102 with the loaded series and also on the images. This identifier will be used to reload the RTSS and RTPL in the same mode, as was defined during planning: the series linked in 4D sequence will be loaded linked, the series loaded separately, even if the same modality will be loaded separately, and not linked in 4D sequences. When the series are linked in 4D sequences, then the user can use the series in 4D cine loop. The system will link the series with same modality and from same patient loaded together, but using the selection from the loaded series table, the user can later redefine the linking.

In a reference series, the first CT series is selected as reference series at load, but later the reference series can be redefined. During load the system will check the compatibility of the series: Ex. Patient ID/Name, Exam ID 1104, series number 1106, geometry of loaded series, orientation, etc. When a problem or mismatch is detected, the user can be warned and has an option to interact with the system, rejecting the loaded series or to continue the loading process. When the series does not match geometrically or the scan orientation differs, a query is made to the user to register geometrically the series to the reference series or to simply reject the series. When the user changes the reference image, then all the contours of the currently defined structures will reference the new reference series.

In template plans, the integrated oncology application will have support for template plans. These template plans help automate the routinely used actions, steps during planning and to automate the steps from the loading to diagnose and planning as much as possible, reducing human interaction whenever possible. The application configuration, the macros (sequence of steps recorded), layout setups, structure names, delineation methods and algorithms and different setup preferences (Ex. Printing, filming, display) will all be saved in the template plans for later use. This information will be saved to the RTPL also. During start-up, the system reloads all the previously saved settings.

In accordance with the DICOM standard, the RT Plan DICOM object references the RTSS object by the UID 1110, and the RTSS DICOM object references the UID 1110 of the images used for treatment plan definition. The DICOM standard provides specifications for generation of UID 1110. UID 1110 uniquely identifies the DICOM objects. In the integrated workflow the system by default will reference all the images used for treatment definition, but will have an option to reference only the images selected for contour definition, to keep the compatibility with systems that do not support this feature yet.

Figure 12:
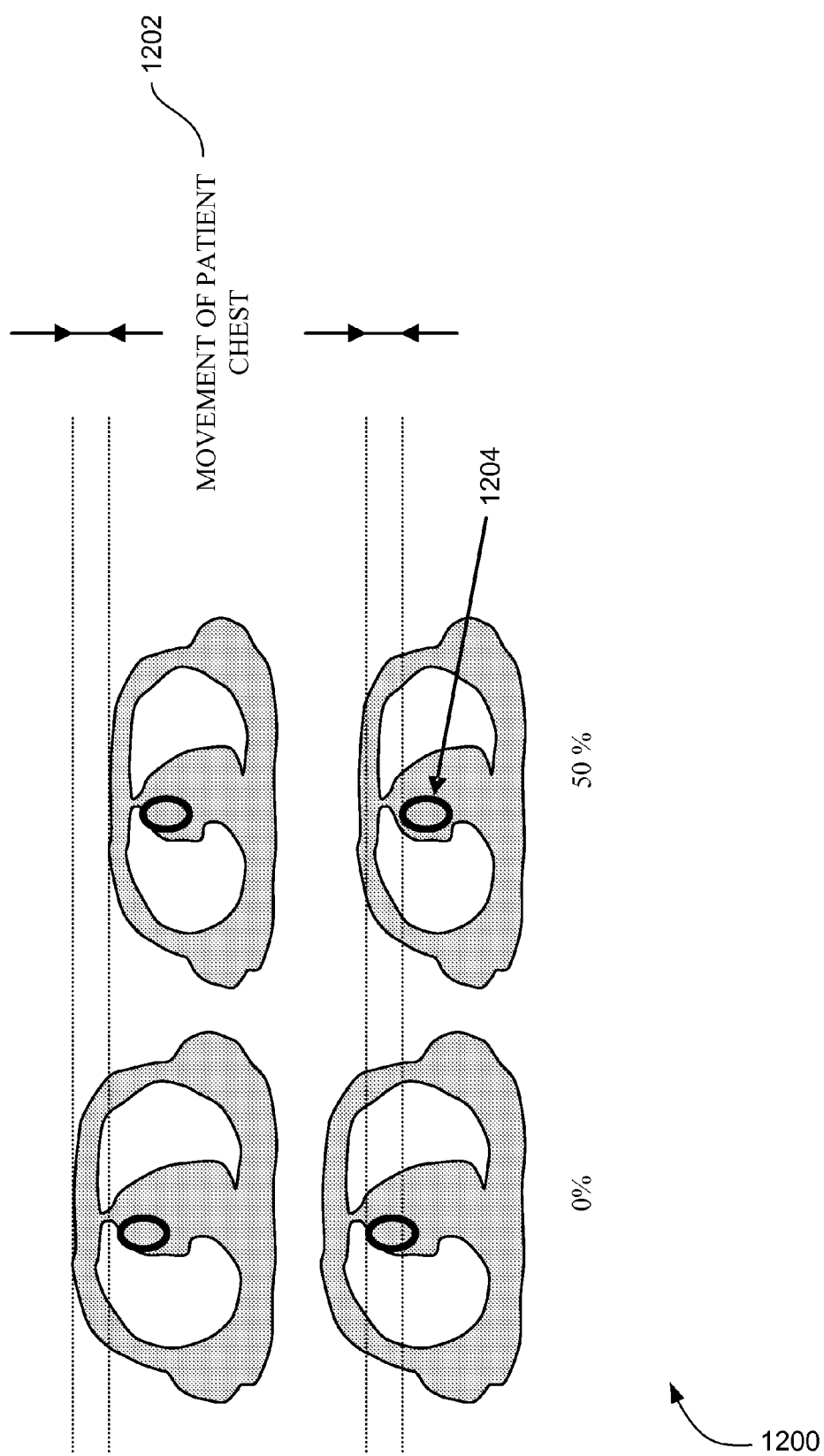
FIG. 12 is a diagram of contour shifting in an images series in respiration, according to an embodiment.

FIG. 12 is a diagram of contour shifting in an images series 1200 in respiration, according to an embodiment. Image series 1200 demonstrates how during movement 1202 of the patient's chest during respiration, a contour is shifted 1204 on phase 50%, after which a user can modify and acknowledge the contour.

Figure 13:
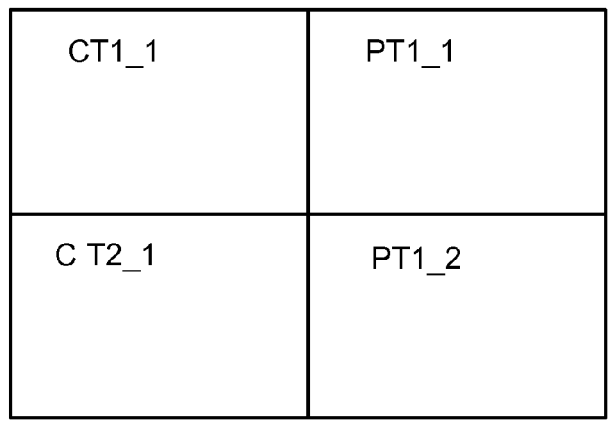
FIG. 13 is a diagram of a view layout setup of an images series in a multi-modality and multi-phase simulation, according to an embodiment.
Figure 13:
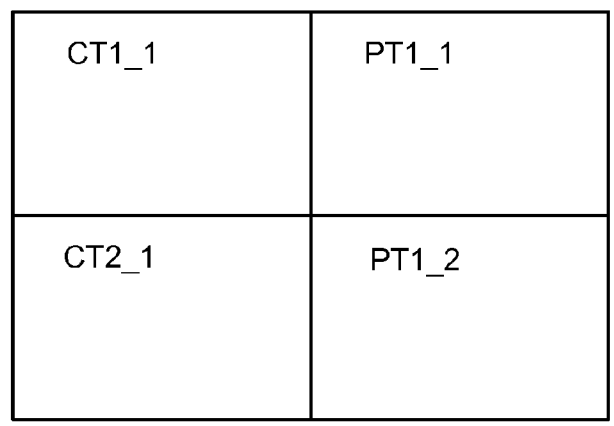

FIG. 13 is a diagram of a view layout setup 1300 of an images series in a multi-modality and multi-phase simulation, according to an embodiment. The view layout setup 1300 demonstrates the benefits of multiple, reference layouts are restored, with all series.

Hardware and Operating Environment

FIG. 14 is a block diagram of the hardware and operating environment 1400 in which different embodiments can be practiced. The description of FIG. 14 provides an overview of computer hardware and a suitable computing environment in conjunction with which some embodiments can be implemented. Embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment.

Computer 1402 includes a processor 1404, commercially available from Intel, Motorola, Cyrix and others. Computer 1402 also includes random-access memory (RAM) 1406, read-only memory (ROM) 1408, and one or more mass storage devices 1410, and a system bus 1412, that operatively couples various system components to the processing unit 1404. The memory 1406, 1408, and mass storage devices, 1410, are types of computer-accessible media. Mass storage devices 1410 are more specifically types of nonvolatile computer-accessible media and can include one or more hard disk drives, floppy disk drives, optical disk drives, and tape cartridge drives. The processor 1404 executes computer programs stored on the computer-accessible media.

Computer 1402 can be communicatively connected to the Internet 1414 via a communication device 1416. Internet 1414 connectivity is well known within the art. In one embodiment, a communication device 1416 is a modem that responds to communication drivers to connect to the Internet via what is known in the art as a "dialup connection." In another embodiment, a communication device 1416 is an Ethernet® or similar hardware network card connected to a local-area network (LAN) that itself is connected to the Internet via what is known in the art as a "direct connection" (e.g., T1 line, etc.).

A user enters commands and information into the computer 1402 through input devices such as a keyboard 1418 or a pointing device 1420. The keyboard 1418 permits entry of textual information into computer 1402, as known within the art, and embodiments are not limited to any particular type of keyboard. Pointing device 1420 permits the control of the screen pointer provided by a graphical user interface (GUI) of operating systems such as versions of Microsoft Windows®. Embodiments are not limited to any particular pointing device 1420. Such pointing devices include mice, touch pads, trackballs, remote controls and point sticks. Other input devices (not shown) can include a microphone, joystick, game pad, satellite dish, scanner, or the like.

In some embodiments, computer 1402 is operatively coupled to a display device 1422. Display device 1422 is connected to the system bus 1412. Display device 1422 permits the display of information, including computer, video and other information, for viewing by a user of the computer. Embodiments are not limited to any particular display device 1422. Such display devices include cathode ray tube (CRT) displays (monitors), as well as flat panel displays such as liquid crystal displays (LCD's). In addition to a monitor, computers typically include other peripheral input/output devices such as printers (not shown). Speakers 1424 and 1426 provide audio output of signals. Speakers 1424 and 1426 are also connected to the system bus 1412.

Computer 1402 also includes an operating system (not shown) that is stored on the computer-accessible media RAM 1406, ROM 1408, and mass storage device 1410, and is and executed by the processor 1404. Examples of operating systems include Microsoft Windows®, Apple MacOS®, Linux®, UNIX®. Examples are not limited to any particular operating system, however, and the construction and use of such operating systems are well known within the art.

Embodiments of computer 1402 are not limited to any type of computer 1402. In varying embodiments, computer 1402 comprises a PC-compatible computer, a MacOS™-compatible computer, a Linux™-compatible computer, or a UNIX®-compatible computer. The construction and operation of such computers are well known within the art.

Computer 1402 can be operated using at least one operating system to provide a graphical user interface (GUI) including a user-controllable pointer. Computer 1402 can have at least one web browser application program executing within at least one operating system, to permit users of computer 1402 to access an intranet, extranet or Internet world-wide-web pages as addressed by Universal Resource Locator (URL) addresses. Examples of browser application programs include Netscape Navigator® and Microsoft Internet Explorer®.

The computer 1402 can operate in a networked environment using logical connections to one or more remote computers, such as remote computer 1428. These logical connections are achieved by a communication device coupled to, or a part of, the computer 1402. Embodiments are not limited to a particular type of communications device. The remote computer 1428 can be another computer, a server, a router, a network PC, a client, a peer device or other common network node. The logical connections depicted in FIG. 14 include a local-area network (LAN) 1430 and a wide-area network (WAN) 1432. Such networking environments are commonplace in offices, enterprise-wide computer networks, intranets, extranets and the Internet.

When used in a LAN-networking environment, the computer 1402 and remote computer 1428 are connected to the local network 1430 through network interfaces or adapters 1434, which is one type of communications device 1416. Remote computer 1428 also includes a network device 1436. When used in a conventional WAN-networking environment, the computer 1402 and remote computer 1428 communicate with a WAN 1432 through modems (not shown). The modem, which can be internal or external, is connected to the system bus 1412. In a networked environment, program modules depicted relative to the computer 1402, or portions thereof, can be stored in the remote computer 1428.

Computer 1402 also includes power supply 1438. Each power supply can be a battery.

Conclusion

A multi-model multi-phase medical imaging system, method and apparatus is described. Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations. For example, although described in procedural terms, one of ordinary skill in the art will appreciate that implementations can be made in an object-oriented design environment or any other design environment that provides the required relationships.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future communication devices, different file systems, and new data types.

The terminology used in this application is meant to include all object-oriented, database, imaging and communication environments and alternate technologies which provide the same functionality as described herein.

We claim:

1. A non-transitory computer-accessible medium having executable instructions capable of directing a processor to:
   generate a spatio-temporal maximum-intensity projection from a respiratory phase separated series of images; generate a phase separated four-dimension series of images of various modalities, generate a radiation therapy structure set, and generate a radiation therapy plan;
   store the spatio-temporal maximum-intensity projection, the respiratory phase separated series of images, the phase separated four-dimension series of images of various modalities, the radiation therapy structure set, and the radiation therapy plan in a memory;
   receive a selection of a custom range of phase separated series of images;
   display a four-dimension phase cine of the custom range of phase separated series having the spatio-temporal maximum-intensity projection;
   identify a desired phase series of images for diagnosis and treatment planning;
   revise the radiation therapy plan based on the identified desired phase series of images; and
   store the radiation therapy structure set and the revised radiation therapy plan in the memory.

2. The non-transitory computer-accessible medium of claim 1, wherein the executable instructions further direct the processor to:
   scan the internal anatomy of a person at a plurality of positions along an axis to obtain scanning data, wherein the scanning at each position is performed over at least one respiratory cycle of the person;
   generate a plurality of cross-sectional digital images based on the scanning data;
   generate a plurality of cross-sectional digital image groups, each group comprising at least two digital images of the plurality of cross-sectional digital images wherein each of the two digital images indicate the internal anatomy at a substantially similar respiratory state;
   generate a plurality of 3-D digital images, wherein each digital image of the plurality of 3-D digital images is determined from a corresponding one of the plurality of cross-sectional digital image groups performing a maximum intensity projection of the plurality of 3-D digital images to obtain a first 3-D digital image;
   generate a boundary within the first 3-D digital image around a predetermined portion of the internal anatomy of the person;
   perform a minimum intensity projection of the predetermined portion of the first 3-D digital image to obtain a second 3-D digital image; and
   combine the first 3-D digital image and the second 3-D digital image to obtain a final 3-D digital image.

3. The non-transitory computer-accessible medium of claim 1, wherein the computer-accessible medium further comprises:
   being a portion of an integrated oncology diagnostic workflow system.

4. The non-transitory computer-accessible medium of claim 1, wherein the executable instructions further direct the processor to:
   load into the memory a raw four-dimension image series of various modalities;
   extract a respiratory phase separated series from the raw four-dimension image series of various modalities;
   load into the memory the respiratory phase separated four-dimension images of various modalities;
   revise the radiation therapy plan based on the respiratory phase separated four-dimension images of various modalities; and
   load into the memory the revised radiation therapy plan.

5. The non-transitory computer-accessible medium of claim 4, wherein the executable instructions further direct the processor to:
   unload the raw four-dimension image series from the memory before the generating the spatio-temporal maximum-intensity projection.

6. The non-transitory computer-accessible medium of claim 4, wherein the executable instructions further direct the processor to load the phase separated four-dimension series of images, load the radiation therapy structure set and load the radiation therapy plan simultaneously.

7. The non-transitory computer-accessible medium of claim 4, wherein
   the various modalities of the raw four-dimension image series further comprise:
   four-dimension computed-tomography and four-dimension positron-emission-tomography.

8. The non-transitory computer-accessible medium of claim 4, wherein
   the extracting further comprises:
   extracting the respiratory phase separated series from the raw four-dimension image series of various modalities based on respiratory motion information from acquired from an external system.

9. The non-transitory computer-accessible medium of claim 5, wherein
   the various modalities of the phase separated four-dimension images further comprise:
   four-dimension computed-tomography, four-dimension positron-emission-tomography, and four-dimension computed-tomography/positron-emission-tomography.

* * * * *